US00PP24808P3

(12) United States Plant Patent
Wheeler et al.

(10) Patent No.: US PP24,808 P3
(45) Date of Patent: Aug. 26, 2014

(54) BLUEBERRY PLANT NAMED 'BB05-58GA-1'

(50) Latin Name: *Vaccinium corymbosum*
Varietal Denomination: BB05-58GA-1

(71) Applicant: Berry Blue, LLC, Grand Junction, MI (US)

(72) Inventors: Edmund J. Wheeler, Holland, MI (US); James F. Hancock, East Lansing, MI (US)

(73) Assignee: Berry Blue, LLC, Grand Junction, MI (US)

( * ) Notice: Subject to any disclaimer, the term of this patent is extended or adjusted under 35 U.S.C. 154(b) by 46 days.

(21) Appl. No.: 13/651,216

(22) Filed: Oct. 12, 2012

(65) Prior Publication Data

US 2014/0109265 P1 Apr. 17, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP9,834 | P | 3/1997 | Lyrene |
| PP10,675 | P | 11/1998 | Lyrene |
| PP11,807 | P2 | 3/2001 | Lyrene |
| PP11,829 | P2 | 4/2001 | Lyrene |
| PP12,165 | P2 | 10/2001 | Lyrene |
| PP15,103 | P3 | 8/2004 | Hancock |
| PP15,146 | P3 | 9/2004 | Hancock |
| PP16,333 | P3 | 3/2006 | Lyrene |
| PP16,404 | P3 | 4/2006 | Lyrene |
| PP18,138 | P3 | 10/2007 | Nesmith |
| PP19,503 | P3 | 11/2008 | Lyrene |
| PP20,027 | P3 | 5/2009 | Lyrene |
| PP21,881 | P3 | 4/2011 | Patel |
| PP22,692 | P3 | 5/2012 | Nesmith |
| PP22,778 | P3 | 6/2012 | Wright et al. |

*Primary Examiner* — Annette Para
(74) *Attorney, Agent, or Firm* — Graybeal Jackson LLP

(57) ABSTRACT

A new and distinct cultivar of blueberry plant named 'BB05-58GA-1' as described and shown herein. 'BB05-58GA-1' is a new and distinct low chill tetraploid Southern highbush (*Vaccinium*) variety of complex ancestry, based largely on *V. corymbosum* with some genes from *V. darrowii, V. angustifolium, V. tenellum* and *V. ashei*. It is a very productive early season ripening variety with very large size, small and dry picking scar, very firm fruit, and high quality fresh market characteristics. Fruit shape is oblate, color is medium blue with medium amounts of sugar and acidity and with a very crunchy and juicy texture. It has storage ability in refrigeration of 2 to 3 weeks.

4 Drawing Sheets

BACKGROUND AND SUMMARY

Blueberries are a well-known fruit enjoyed by many throughout the world. One example of an existing, patented blueberry variety is Star, U.S. Plant Pat. No. 10,675. Another example of an existing, patented blueberry variety is Rebel, U.S. Plant Pat. No. 18,138.

Compared to Star, the present cultivar, 'BB05-58GA-1', is 7-10 days earlier ripening; has much larger berry size and a flattened shape; is 3 weeks earlier to bloom; the fruit cluster is not as loose as Star; and, the leaves are larger and wider.

Compared to Rebel, the maturity of 'BB05-58GA-1' is 3-5 days earlier than Rebel; the bush shape is more upright and less spreading; the flowering is 2 weeks earlier; the leaves are dark green, larger, and more round; and, the fruit size is appreciably larger, shape is more flat.

The present cultivar, 'BB05-58GA-1', provides one or more advantages compared to these and/or other blueberry varieties.

BRIEF DESCRIPTION OF THE PHOTOGRAPHS

DETAILED DESCRIPTION

Figure 1:
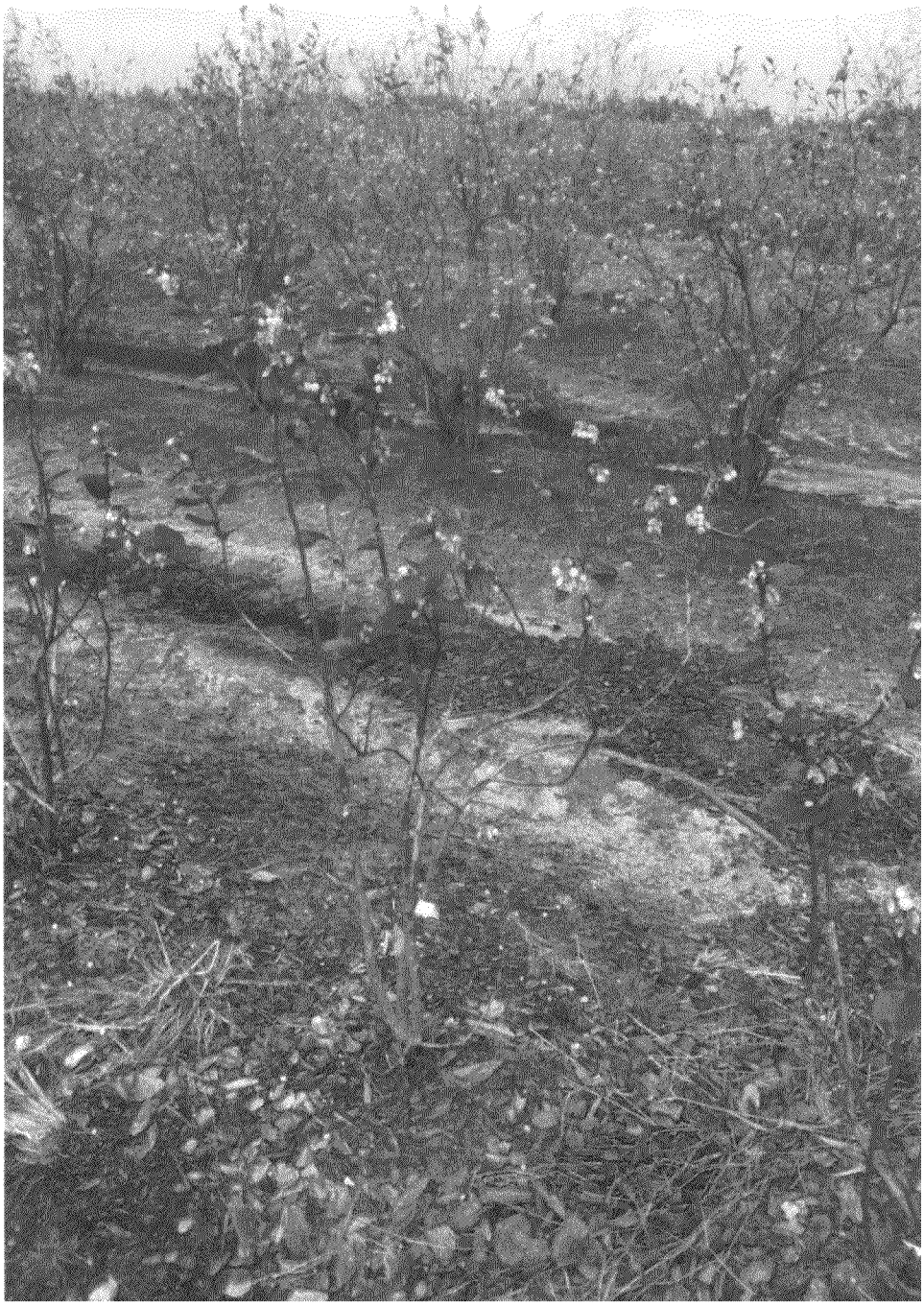
FIG. 1 is a photograph taken in February 2012 of the Blueberry cultivar 'BB05-58GA-1', showing the bush at flowering, and showing cane growth, flower cluster and crown size.
Figure 2:
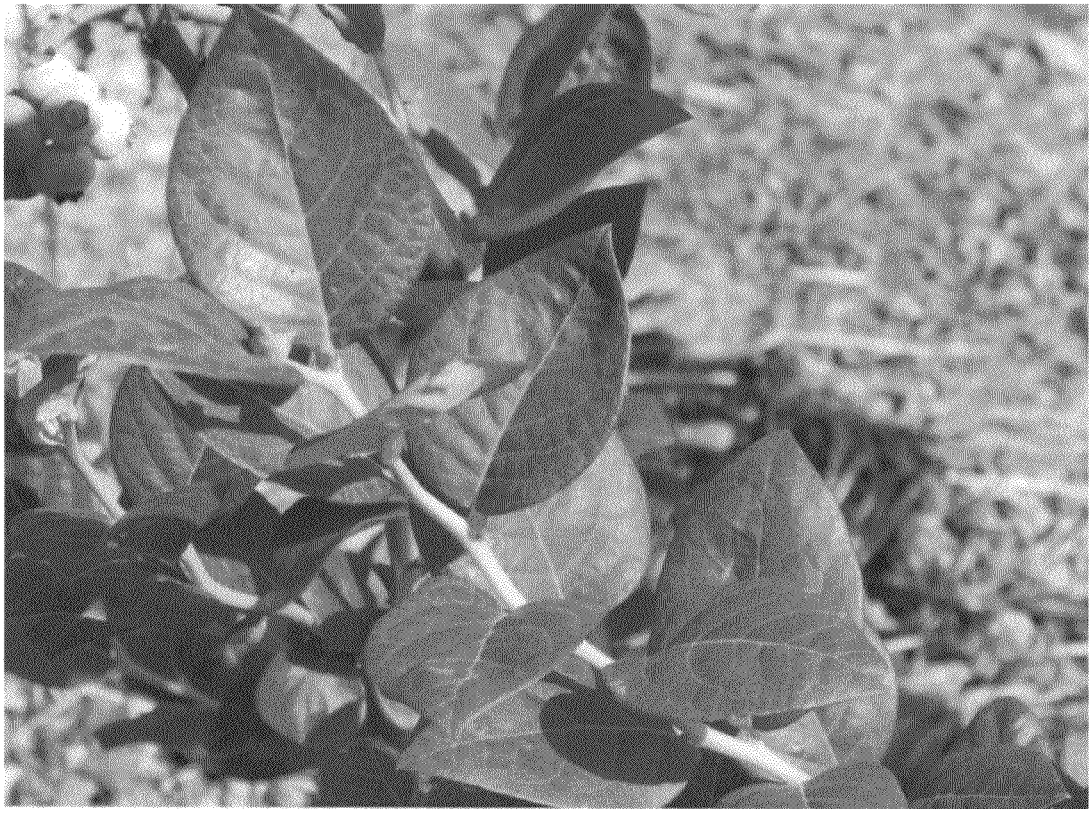
FIG. 2 is a photograph taken in April-May 2012 of the Blueberry cultivar 'BB05-58GA-1', showing leaf shape and color, venation, new wood color, petiole size and color.
Figure 3:
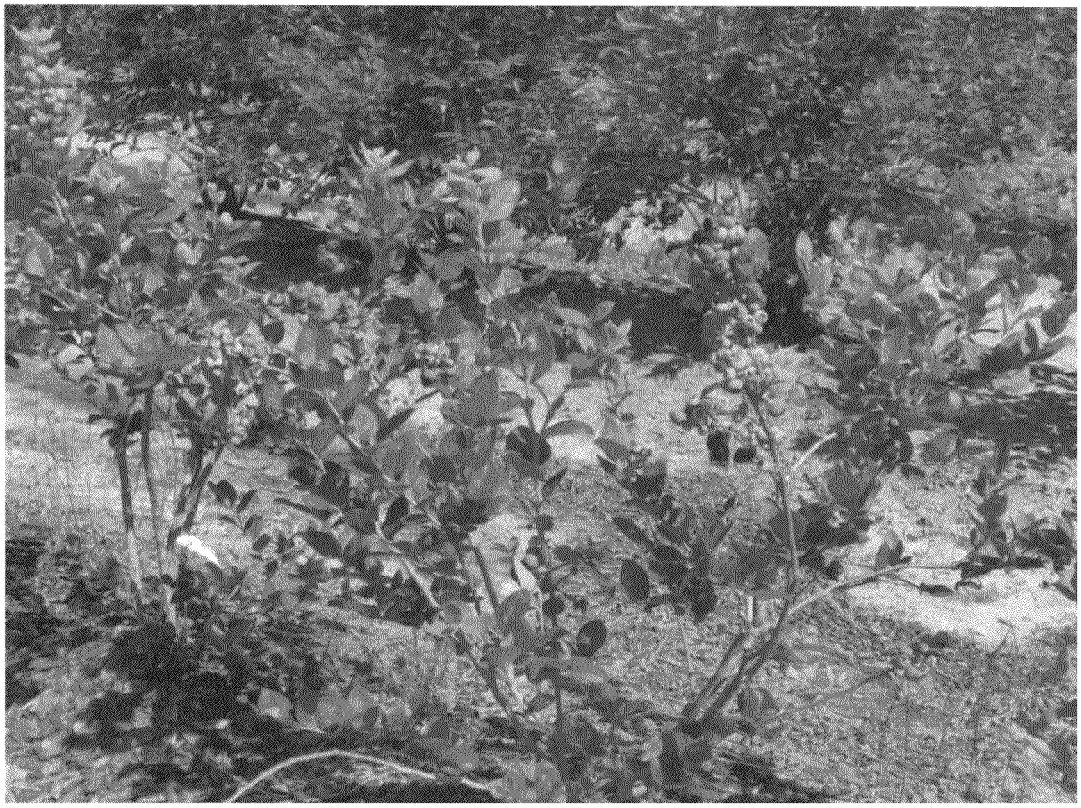
FIG. 3 is a photograph taken in April-May 2012 of the Blueberry cultivar 'BB05-58GA-1', showing a 3 year old bush with ripe and unripe fruit, and also showing bush shape, size and color of ripe and unripe fruit, fruit cluster density, fruit presentation.
Figure 4:
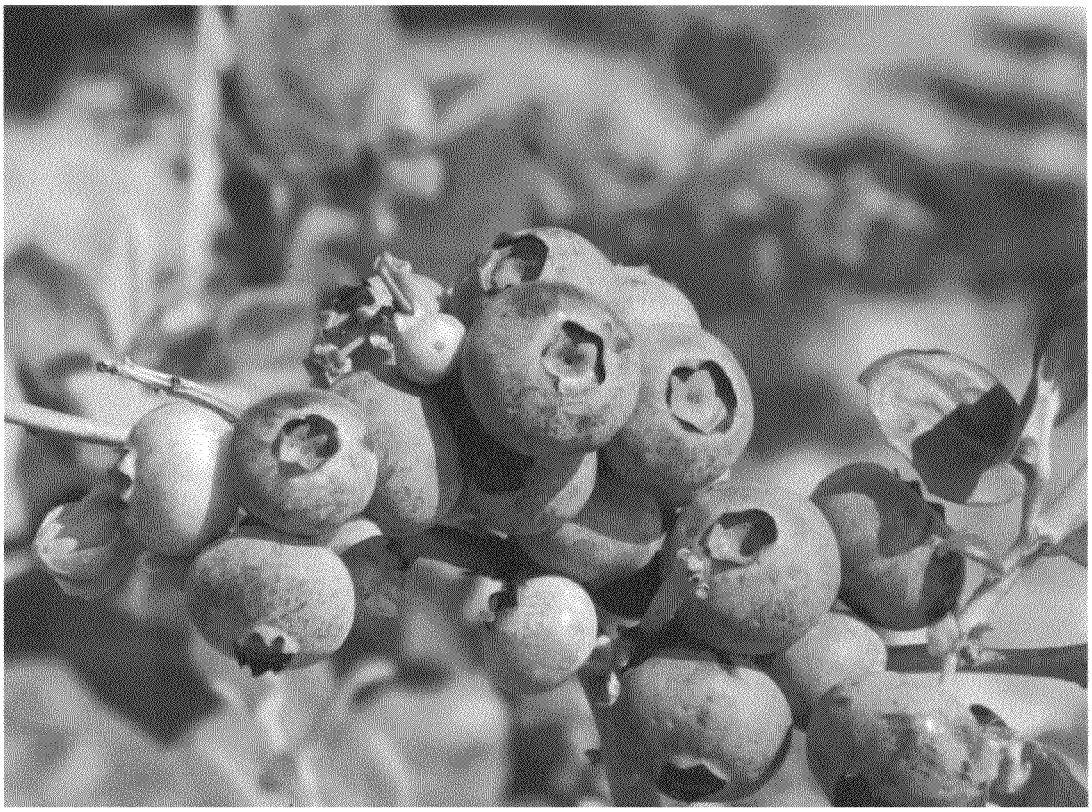
FIG. 4 is a photograph taken in May 2012 of the Blueberry cultivar 'BB05-58GA-1', showing a Photo of close-up of ripe and unripe fruit, showing size, shape, colors, calyx size and ridging, bloom and cluster density

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely from specimen plants grown near Manor, Ga. Data were obtained on plants that were 3 years old.

Cultivar name: 'BB05-58GA-1'.

Classification:

*Family*.—Ericaceae.

*Botanical name*.—*Vaccinium corymbosum*.

*Common name*.—Blueberry.

Parentage:

*Female parent*.—Name: Draper (Duke unpatented× G751 unpatented). U.S. Plant Pat. No.: 15,103. Compared to Draper, 'BB05-58GA-1' has a much lower chill requirement (800 vs. 400) and is adapted to a lower chill area production while Draper is not. 'BB05-58GA-1' produces more canes, has a later maturity difference of 6-8 weeks, has a larger berry with a more flattened shape, and has a more rounded larger leaf than Draper.

*Male parent*.—Emerald (FL91-69 unpatented×NC1528 unpatented). U.S. Plant Pat. No.: 12,165. Compared to Emerald, 'BB05-58GA-1' requires more chill hours (200 vs. 400), has 10 days later maturity, has a more concentrated ripening, and has flowers that are more bell-shaped. The bush shape of 'BB05-58GA-1' is more upright and the berry size is larger than Emerald.

'BB05-58GA-1' was created from a cross made in 2005 in a South Haven, Mich., greenhouse. Seeds from the cross were sown and plants were grown for 1 year in Grand Junction, Mich. and then planted in a seedling evaluation plot in 2006 near Manor, Ga. The plant was first selected in the spring of 2007 based on improved and excellent fruit and morphological characteristics. The individual bush was evaluated in successive years through 2009, exhibiting an excellent performance of earliness, very large berry size, and very good fruit quality. Several multi-bush trials were established near Interlachen, Fla., Manor, Ga., Homerville, Ga., and Baxley, Ga. in 2011. Two 250 bush plots were established in 2011 near Manor, Ga. In all of these bushes and trials, the characteristics of the original selection have been retained.

'BB05-58GA-1' was first asexually propagated by softwood cuttings in 2008 and rooted in Grand Junction and Manor, Ga., as well as in succeeding years. Several hundred plants have also been propagated by tissue culture. In all cases, the propagated plants have retained the original characteristics. The variety roots readily from softwood cuttings and tissue culture microshoots.

All field observations were made in Spring 2012 on 3-year old plants located in a trial near Manor, Ga., from plants propagated from the original bush selection. Laboratory analysis of fruit characteristics were done in Grand Junction, Mich.

General comments: 'BB05-58GA-1' is a new and distinct low chill tetraploid Southern highbush (*Vaccinium*) variety of complex ancestry, based largely on *V. corymbosum* with some genes from *V. darrowii, V. angustifolium, V. tenellum* and *V. ashei*. It is a very productive early season ripening variety with very large size, small and dry picking scar, very firm fruit, and high quality fresh market characteristics. It is intended for areas which successfully grow lower chill Southern highbush varieties. The fruit are very large, typically 3-4 grams each, and are well exposed on a vigorous medium upright bush with a medium-size crown. The date of 50% flowering in Southeast Georgia is about February 5. Winter chilling requirement for successful flowering and leafing is approximately 400 hours (<7° C.). Bush growth is vigorous. Flowering and leafing are synchronous. Frost protection may be needed for successful pollination and fruit set. Fruit are very large with ripening of 50% of the fruit usually by May 1 in Southeast Georgia. Fruit shape is oblate, color is medium blue with medium amounts of sugar and acidity and with a very crunchy and juicy texture. It has storage ability in refrigeration of 2 to 3 weeks. Thus, provides a very large fruit size and earliness of ripening season, and a very firm berry for such a large fruit with a crunchy, sweet texture and flavor.

References to color refer to The Pantone Book of Color, Eisemann and Herbert, Harry N. Abrams, Inc. Publishers, New York, ISBN 0-8109-3711-5, 1990.

No spectrographic device was used to take color readings.

Morphological characteristics reference: Plant Systematics, Jones and Luchsinger, 2 Ed., McGraw Hill, New York, ISBN 0-07-032796-3, 1986.

Firmness readings—BioWorks FirmTec2, Wamena, Kans.

Average size information:

*General description*.—Medium large bush, medium upright, 3-year plant 130 cm height, 100 cm width, height/width ratio 1.3:1.

*Growth*.—Very good.

*Productivity*.—Very good.

*Cold hardiness*.—Leaf and flower buds −5° C., open flowers and fruit −2° C.

Specific features of the variety:

Plant:

*Growth habit*.—Medium upright.

*Plant width*.—100 cm at mid-bush.

*Plant height*.—130 cm.

*Spread*.—Canopy 100 cm.

*Productivity*.—5-6 lbs per mature bush.

*Cold hardiness/tolerance*.—Leaf and flower beds −5° C., flowers and fruit −2° C.

*Chilling requirement*.—400 hours below 7° C.

*Canes*.—Modestly branched, 5-6 canes/bush, 70-90 cm length, medium number of laterals. Mature cane color — Pantone Stucco, 16-1412, texture — rough.

*Fruiting wood*.—Smooth, immature winter color — Pantone Barn Red 18-1531; immature summer color — Pantone Willow Green 15-0525.

*Internode length range*.—16-20 mm, average 18 mm.

*Surface texture of new wood*.—Smooth, mature canes — circular, 18 mm width.

*Time of beginning of leaf bud burst* (*include location*(*s*)).—January 21 (Manor, Ga.).

*Time of beginning of flowering* (*include location*(*s*)).—January 25 (Manor, Ga.).

*Time of fruit ripening* (*include location*(*s*)).—May 1 (Manor, Ga.).

*Disease resistance/susceptibility*.—None claimed.

Foliage:

*Leaf color*.—Upper — Pantone Grass Hopper 18-0332; lower — Pantone Sage 16-0421.

*Leaf arrangement*.—Alternate.

*Shape*.—Ovate elliptic.

*Leaf margins*.—Entire.

*Leaf venation*.—Pinnate.

*Leaf apices*.—Acute.

*Leaf bases*.—Cuneate.

*Vein and petiole colouration*.—Pantone Willow Green 15-0525.

*Petiole length*.—3 mm.

*Leaf dimensions*.—Overall shape: 60 mm-72 mm, average 68 mm. Width: 46 mm-52 mm, average 50 mm.

*Leaf margins*.—Entire; no pubescence or nectaries.

*Leaf surface*.—Upper — small hairs on midrib and larger veins; Lower — none.

Flower:

*Flower shape*.—Urceolate.
*Flower bud number*.—Medium high.
*Flowers per cluster*.—7-8.
*Flower fragrance*.—Floral similar to hyacinth.
*Corolla color*.—Pantone Bone White 12-0105.
*Corolla length*.—7 mm.
*Corolla aperture width*.—5 mm.
*Flower peduncle*.—Length 5 mm.
*Color*.—Pantone Parrot Green 15-0341.
*Flower pedicel*.—5 mm.
*Color*.—Pantone Parrot Green 15-0341.
*Calyx* (*with sepals*).—2 mm.
*Color*.—Pantone Parrot Green 15-0341.
*Stamen*.—Length: 7 mm.
*Number per flower*.—10.
*Filament color*.—Pantone Narcissus 16-0950.
*Style*.—8 mm, top of ovary to stigma tip.
*Color*.—Pantone Endive 16-0632.
*Pistil*.—7 mm.
*Ovary color*.—Pantone Endive 16-0632.
*Anther*.—Length: 3 mm.
*Number*.—10/flower.
*Color*.—Pantone Narcissus 16-0950.
*Pollen*.—Abundance: medium. Color: Pantone Antique White 11-0105.

Fruit:

*Date of* 50% *maturity*.—May 1 (Manor, Ga.).
*Yield*.—5-6 lbs/bush.
*Berry color*.—With wax: Pantone Star Sapphire 18-4041. With wax removed: Pantone Blue Indigo 19-3928.
*Berry flesh color*.—Pantone Frozen Dew 13-0513.
*Berry surface wax abundance*.—Medium, persistent.
*Calyx*.—Width — 9 mm; depth — 2 mm; shape — 5 lobed with medium height ridges.
*Berry weight*.—3.6 grams/berry.
*Berry size diameter*.—22 mm width, 13 mm height, Aspect (H/W) — 0.6.
*Berry shape*.—Oblate.
*Fruit stem scar*.—Small (1 mm), dry.
*Cluster density*.—Medium.
*Detachment force*.—Medium.
*Self-fruitfulness*.—Fair, will need cross pollination for maximum yield, earliness, and size.
*Berry firmness*.—Firm, FirmTec 2 score — 228 g/mm$^2$.
*Berry sweetness*.—Medium, Brix° 10.3.
*Berry acidity*.—Medium, TA — 0.54.
*Berry flavor and texture*.—Very good with balanced sweetness and acidity, crunchy and juicy.
*Suitability for mechanical harvesting*.—Some potential, but may be difficult with fruit size, detachment, and cluster density.

Seed:

*Seed abundance in fruit*.—Medium low.
*Seed color*.—Pantone Paprika 17-0553.
*Seed dry weight*.—NA.
*Seed size*.—Large 1.5-2.0 mm.

Possible typical market uses: Fresh market, processing into jams, puree, yogurt.

Storage quality: Medium, 2-3 weeks in refrigerated storage.

What is claimed is:

1. A new and distinct cultivar of Blueberry plant named 'BB05-58GA-1' as described and shown herein.

* * * * *